United States Patent

Gancet et al.

[11] Patent Number: 5,885,263
[45] Date of Patent: Mar. 23, 1999

[54] SUPERABSORBENT COMPOSITION INTENDED FOR THE PRODUCTION OF SANITARY ARTICLES OF THE UNDERWEAR, DIAPER OR DISPOSABLE DIAPER TYPE WHICH DO NOT DEVELOP UNPLEASANT SMELLS

[75] Inventors: Christian Gancet, Lons; Nathalie Cuny, Carrieres/Seine; Monique Lescure, Pau; Jean-Louis Seris, Jurancon, all of France

[73] Assignee: Elf Atochem S.A., Puteaux, France

[21] Appl. No.: 634,716

[22] Filed: Apr. 18, 1996

[30] Foreign Application Priority Data

Apr. 18, 1995 [FR] France ................... 95 04584

[51] Int. Cl.$^6$ ............... B32B 5/16; A61F 13/15
[52] U.S. Cl. ............ 604/359; 604/360; 604/368; 424/489; 428/402; 428/403
[58] Field of Search ................ 604/359, 360, 604/368; 428/402, 403; 424/489

[56] References Cited

U.S. PATENT DOCUMENTS

| | | |
|---|---|---|
| 1,935,170 | 11/1933 | Woody et al. . |
| 1,953,526 | 4/1934 | Ainslie et al. . |
| 4,333,461 | 6/1982 | Muller . |
| 4,363,322 | 12/1982 | Andersson . |
| 4,624,868 | 11/1986 | Muller . |
| 4,641,605 | 2/1987 | Gordon ........................ 119/1 |
| 4,992,326 | 2/1991 | Dabi ........................ 428/283 |
| 5,183,010 | 2/1993 | Raymond et al. ............ 119/172 |
| 5,183,655 | 2/1993 | Stanislowski et al. ....... 424/76.7 |
| 5,230,958 | 7/1993 | Dabi ........................ 428/402 |

FOREIGN PATENT DOCUMENTS

| | | |
|---|---|---|
| 0 164 818 | 12/1985 | European Pat. Off. . |
| 61 179 155 | 8/1986 | Japan . |
| WO 94/25077 | 11/1991 | WIPO . |

*Primary Examiner*—John G. Weiss
*Assistant Examiner*—Dennis Ruhl
*Attorney, Agent, or Firm*—Pennie & Edmonds LLP

[57] ABSTRACT

Compositions which greatly diminish, or eliminate, unpleasant smells associated with the use of underwear and diapers are described. These compositions are composed of superabsorbent polymers of the polyacrylic type and of certain boron derivatives, in particular sodium tetraborate. The sanitary articles which incorporate these compositions do not develop unpleasant smells, ammoniacal or otherwise.

2 Claims, No Drawings

SUPERABSORBENT COMPOSITION INTENDED FOR THE PRODUCTION OF SANITARY ARTICLES OF THE UNDERWEAR, DIAPER OR DISPOSABLE DIAPER TYPE WHICH DO NOT DEVELOP UNPLEASANT SMELLS

The invention relates to the production of sanitary articles intended to absorb and retain body fluids.

When the absorbing article in place is impregnated with such body fluids, in particular urine, powerful and unpleasant smells are produced. The predominant smells among these are ammoniacal smells due to the ammonia originating from the hydrolysis of urea by the ureases of bacteria (Proteus, Acinetobacter, and the like) present on the skin and in the digestive tract.

For the purpose of suppressing these smells, widespread recourse has been had to absorbents of smells or ammonia (U.S. Pat. No. 3,340,875, Scott Paper Company), optionally in combination with deodorants, fragrances, and the like. The use of pH buffers (WO-A-94 25077), of oxidants (hydrogen peroxide, chlorine dioxide), of biocides (metals or of metal cations), as well as of bactericides (quaternary ammoniums, in particular), of antibiotics, of complexing agents or of surfactants, both alone and in combination with one another, has also been recommended. These various products present the general problem of an irritant effect on the skin and mucosal mebranes. Absorbents of smells or of ammonia are certainly less dangerous in this respect but they leave the field free for a bacterial growth which remains worrying and which it would be advisable to control from the outset. The way which appeared necessary for the control of the bacterial emission of ammonia from urea consists in inhibiting the enzymes which are responsible for it, that is to say the ureases.

The use of urease inhibitors of low or moderate activity has until now only been envisaged in combination with ammonia scavengers (JP 61-179155). Some powerful urease inhibitors, such as hydroxamic acid derivatives (U.S. Pat. No. 3,920,015, Allied Chem. Corp.), are advantageous but their toxicity excludes them from the targeted use. Others, such as phenyl phosphorodiamidate (PPDA) or dimethyldithiocarbamate (DTC), are compounds which are very effective against the formation of ammonia but give rise, during their use, to other very unpleasant sulfurous or alliaceous smells which are perhaps related, at least in part, to their own decomposition by the bacterial flora present.

The search for a solution to this problem is all the more pressing since, nowadays, the absorption capacity for body fluids of protection articles has been very substantially increased by incorporating superabsorbent polymers (SAP) into them, in particular hydrophilic polymers and copolymers of acrylic acid, and since, by the same token, the time during which they are maintained in place has been increased, all conditions which promote the development of microbial and enzymatic activity and of the smells which result therefrom.

It has now just been found that it is possible to formulate superabsorbent polymers with certain boron derivatives in order to prepare therefrom compositions which, although impregnated with urine or with biological fluids containing it and maintained under conditions of use which are especially propitious for bacterial growth, give rise neither to significant evolution of ammonia nor to repellent or simply unpleasant smells and which communicate this property to the sanitary articles which contain them.

The invention thus consists of a superabsorbent composition intended for production of sanitary articles of the underwear, diaper or disposable diaper type which do not develop unpleasant smells which comprises a polymer, which is superabsorbent with respect to water, saline solutions and body fluids, and sodium tetraborate or sodium metaborate in the proportion of 0.1 to 10% of boron derivative, preferably 0.5 to 5%, with respect to the superabsorbent composition.

Superabsorbent polymers within the meaning of the present invention are polymers which result from the polymerization, with partial crosslinking, of watersoluble ethylenically unsaturated monomers, in particular acrylic and methacyrlic acids and their alkaline salts, whether they are obtained by an inverse suspension or solution polymerization process. These polymers possess a very high capacity for absorption and retention of water and aqueous solutions and are nowadays widely available commercially in the form of powders with particle sizes of between 100 and 800 $\mu$m. The literature relating to them is very extensive; reference may be made, for example, to EP-A-0,312,952 (The Dow Chem. Co.) and to EP-A-0,441,507 (Sumitomo Seika Chem.).

Within the meaning of the present invention, sodium tetraborate ($Na_2B_4O_7$) is the anhydrous, pentahydrate or decahydrate (borax) salt and the metaborate ($NaBO_2$) is also regarded independently of its degree of hydration. These boron compounds are mixed with the polymer in the powder form in proportions indicated above.

The preparation of the composition according to the invention is very easy, since it is sufficient to incorporate the boron derivative in the powder form, preferably with a particle size also of between 100 and 800 $\mu$m, in the superabsorbent polymer powder by simple mixing. However, it has been observed that, if the boron derivative was introduced within the superabsorbent polymer particles, an odor-preventing efficiency was obtained, at equivalent concentration, which is greater than by simple mixing of the powders. This results in an alternative form of the process, which also forms part of the invention, whereby the polymer powder is swollen using an aqueous solution of boron derivative and then the water thus introduced is evaporated.

The superabsorbent compositions of the invention become gelled on contact with water, aqueous saline solutions or body fluids, like the superabsorbents of the prior art, and the gels thus formed behave in a substantially identical way. They do not suffer from any counterindication, the boron derivatives which are the means of the invention being rightly regarded as inoffensive and being widely used in various mild antiseptic compositions at contents of the order of 1% by weight. They are used in place of the ordinary superabsorbents in the manufacture of sanitary articles such as disposable diapers for babies, for young children, for adults or for elderly people of both sexes. This use also constitutes a subject of the present invention.

Assessment of the true effectiveness of odor-preventing products is difficult to carry out. Since the invention comes within the context of urease inhibitors, the candidate compounds which can be envisaged for their anti-urease activity are therefore generally classified by an $IC_{50}$ value according to the results of an enzymatic test which will be described later. Since the process which generates smells is a biological process, it is necessary to be able to estimate the effectiveness of various urease inhibitors for their ability to limit the biological emission, by urea-fermenting microorganisms, of at least the most common odorous compound, in this case ammonia. This effectiveness is understood of the inhibitor just as it is or in the presence of various substances with which it is combined in the production of diapers and other sanitary articles, in particular superabsorbent polymers. The results of this test correlate fairly well with the $IC_{50}$ values. Finally and particularly, it is necessary to be able to decide on the satisfactory overall result by olfative tests under conditions which give acceptable simulation of the conditions of use of the products in which the superabsorbent composition which is believed to inhibit smells is incorporated. They are carried out by impregnating a disposable diaper with urine under standardized conditions, by heating the combination in an oven at a low temperature and by subjecting the object to a nose panel for overall assessment of its possible unpleasant smells.

Such tests are described in the examples given below, which illustrate the unexpected effectiveness of the products according to the invention. In these tests, the superabsorbent polymer used is a partially neutralized polyacrylic acid marketed under the name of AquaKeep®D (Elf Atochem S.A.).

EXAMPLE 1

$IC_{50}$ Values of several molecules believed to operate as urease inhibitors.

The test comprises the decomposition of a neutral solution of urea at 1 g/l (0.016M) in a 0.1M triethanolamine buffer, to which solution has or has not been added the compound whose anti-urease activity it is desired to estimate, by a solution of soybean urease (1500 U from Sigma) at 1 mg/ml in the buffer+10 mM of glutathion under the following conditions. 400 µl of urease solution 10 and 10 ml of urea solution are mixed. The mixture is maintained at 37° C. 1 ml samples are taken with time and assayed for $NH_3$ by the Kessler method: each 1 ml sample is added to 24.5 ml of dilute Nessler reagent (0.5 for 24) and, after incubating for 10 minutes, the absorbance at 425 nm in measured. An $IC_{50}$ value is determined, which value is the concentration of inhibitor in the mixture, expressed as µM, capable of reducing the ureaue activity by 50% under the conditions of the test.

The $IC_{50}$ values for several urease inhibitors known in the literature are reported in the following table.

| Compound | $IC_{50}$ (µM) |
| --- | --- |
| Phenyl phosphorodiamidate (PPDA) | 0.05 |
| Boric acid | 450 |
| Sodium metaborate | 260 |
| Sodium tetraborate 5H$_2$O | 160 |
| Sodium pyrophosphate | 8000 |
| Hydroquinone | 500 |
| Dimethyldithiocarbamate (DTC) | 10 |
| Salicylhydroxamic acid | 310 |
| Glycolic acid | 450 |
| Acetohydroxamic acid | 600 |
| Nitrilotriacetic acid | 5000 |

EXAMPLE 2

SAP/sodium tetraborate pentahydrate synergy

The $IC_{50}$ value is determined as described above. The tests are carried out by comparison both with a control medium and with media containing respectively solely SAP, sodium tetraborate pentahydrate ($Na_2B_4O_7.5H_2O$) and SAP to which has been added 3.9% by weight of sodium tetraborate pentahydrate, which was obtained by mixing 29 kg of $Na_2B_4O_7.5H_2$ O with 718.5 kg of superabsorbent polymer, so as finally to obtain 750 kg of borate-containing composition. The results are reported in the following table.

| Composition | Residual urease activity % |
| --- | --- |
| Control (without SAP and without inhibitor) | 100 |
| SAP alone (10 mg/15 ml of medium) | 100 |
| SAP alone (100 mg/15 ml of medium) | 100 |
| Borate-containing SAP (10 mg/15 ml of medium) | 50 |
| Borate-containing SAP (100 mg/15 ml of medium) | 0 |

The effectiveness of the borate-containing SAP is clearly demonstrated by the test.

It was noted that the curve of the urease activity as a function of the additive-containing SAP content in the medium was a smooth curve. Under these conditions, the point of 50% residual urease activity for this SAP containing 3.9% of tetraborate pentahydrate can be interpreted in terms of $IC_{50}$ with respect to the tetraborate and is calculated at 90 µM. This figure will be compared with the value of 160 µl for the tetraborate pentahydrate alone in the table in Example 1 in order to observe that the $IC_{50}$ which can be attributed to sodium tetraborate pentahydrate in the presence of SAP is superior to that which is calculated with the tetraborate alone. This synergic effect between the SAP and the tetraborate with respect to its anti-urease activity is most unexpected and remains unexplained.

EXAMPLE 3

Inhibiting effect on formation of ammonia.

The introduction is carried out, into a 100 ml Erlenmeyer flask equipped (cf. FIG. 1) with a Prolabo No. 02.436.112 ① measuring tube (these are graduated glass tubes containing a reagent for ammonia which changes from violet to yellow, the position of the demarcation between the two colorings giving an indication of the amount of ammonia evolved), of urine ② and of a mixture of defibrated cellulose pulp and of SAP ③ in the following proportions:

| | |
| --- | --- |
| fresh urine | 50 ml |
| fermented urine (inoculum) | 2 ml |
| superabsorbent | 0.5 g |
| defibrated cellulose pulp (fluff) | 0.5 g |

The inoculum is necessary because the fresh urine is sterile. This inoculum is prepared in the following way: 0.25 g of urea and 1 g of soiled fluff originating from a used baby disposable diaper are added to 100 ml of fresh urine (for greater convenience, the medium could be inoculated with, in place of the used fluff, a strain of Bacillus, Proteus or Acinetobacter). This solution, withdrawn after 24 hours at room temperature, constitutes the inoculum.

In this test, the odor inhibitor is not introduced separately, but with the superabsorbent formulated as indicated above and with a content in the superabsorbent such that its dose in the medium to be fermented is 10 times its $IC_{50}$.

The system is left for 18 hours at 40° C., after which the position of the region of transition of violet/yellow coloring in the measuring tube is noted, which thus provides a comparative estimation of the evolution of ammonia and thus of the influence on this evolution of the products which have been subjected to the test. After this, the Erlenmeyer flask is carefully opened and the experimenter gives his assessment of the smell of the contents. The results are recorded in the table below.

| Substrate/inhibitor | Reading an the measuring tube | Smell |
|---|---|---|
| Control (neither SAP nor inhibitor) | >500 | Strong ammoniacal |
| SAP alone | >500 | Strong ammoniacal |
| SAP + $Na_2B_4O_7.5H_2O$ | 90 | No perceptible ammonia smell. Neutral smell of fresh urine |
| SAP + PPDA | 120 | Unpleasant smell of rotten cabbage |
| SAP + DTC | 1070 | Unpleasant smell of rotten cabbage |
| SAP + hydroquinone | 120 | Slight nauseating |

EXAMPLE 4

Comparative test of an odor-preventing treatment by mixing powders or by impregnation.

The introduction is carried out, in the device of Example 3, of a synthetic urine inoculated by *B. pasteurii* (ATCC 11859) and of a mixture of defibrated cellulose pulp and of SAP containing 4% borax, one being produced by mixing SAP and borax powders and the other by impregnation of SAP by the necessary amount of aqueous borax solution at 80° C. (22% by weight solution). The comparative amounts of NH3 evolved (in ppm) at different moments are reported below:

| t (hours) | SAP alone | SAP + 4% borax powder | SAP + 4% borax solution |
|---|---|---|---|
| 0 | 0 | 0 | 0 |
| 6 | 7 | 7 | 7 |
| 9 | 20 | 18 | 10 |
| 10 | off the scale | 24 | 12 |
| 30 | off the scale | off the scale | 13 |

These results show the advantage, particularly with respect to relatively long time periods, of tetraborate impregnation compared with simple mixing.

EXAMPLE 5

The test is carried out by using, as substrates, disposable diaper material not containing SAP. Such a blank disposable diaper, with a size of 31×11 cm, is taken and opened and 4 grams of SAP are spread over it over a surface area of approximately 15×9 cm. The centre of the disposable diaper is moistened with a mixture of 50 ml of fresh urine and 2 ml of inoculum. The disposable diaper is enclosed in a plastic bag which is welded. The whole assembly is placed in a ventilated oven at 37° C. for 12 hours. At the end of this period, the bag is opened and an estimation of the smell is made by a nose panel (8 people). In a system of notation which confers the grade 0 in the complete absence of smell to 5 for a very strong smell of ammonia, the following are obtained:

| Control disposable diaper | 4.6 |
|---|---|
| Disposable diaper with ordinary SAP | 4.6 |
| 4% of "powder" borax | 3.3 |
| 4% of "liquid" borax | 2.8 |

There has thus been found:

a strong smell of ammonia with the control disposable diaper, a strong smell of ammonia with the disposable diaper carrying an ordinary polyacrylic superabsorbent, no smell of ammonia with the disposable diaper with a polyacrylic superabsorbent containing 3.9% of sodium tetraborate pentahydrate.

A test of the same type, carried out with a synthetic urine, confirms, with greater clarity, the above results:

| Control disposable diaper | 5 |
|---|---|
| Disposable diaper with ordinary SAP | 5 |
| 4% of "powder" borax | 4 |
| 4% of "liquid" borax | 3 |

SINGLE PLATE
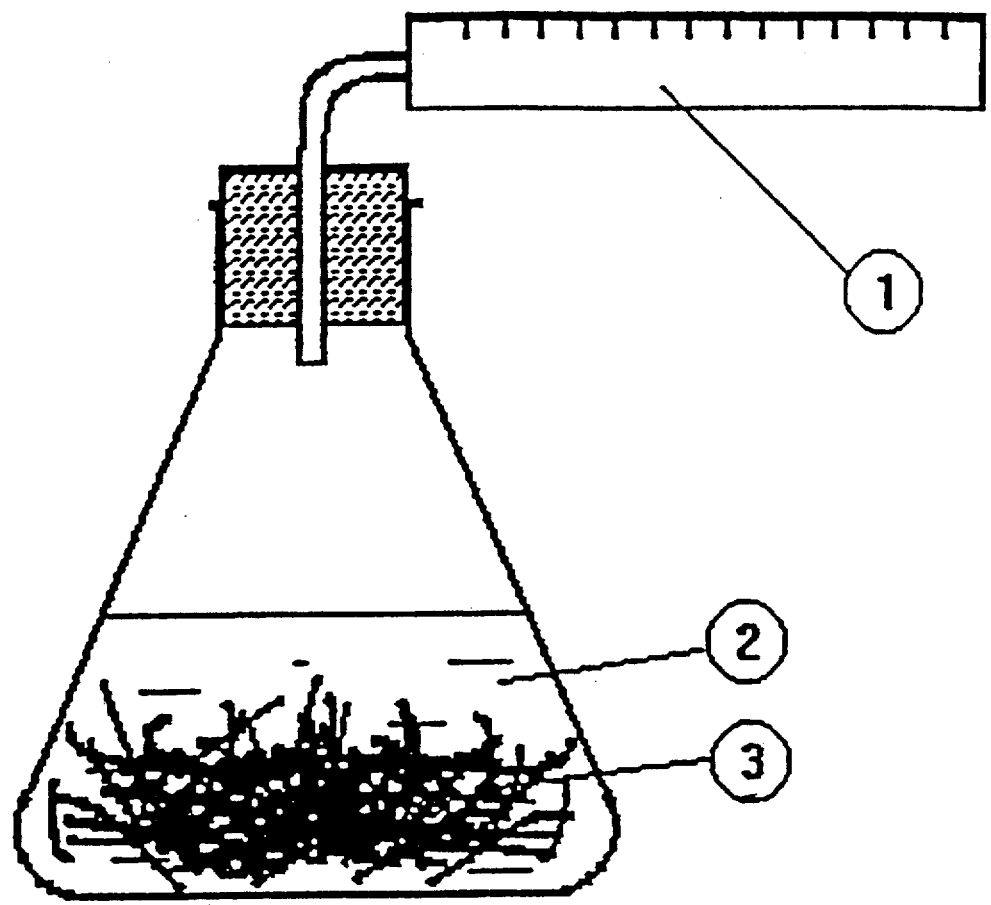

We claim:

1. A process for the production of a superabsorbent composition intended for the production of sanitary articles selected from the group consisting of underwear, diapers and disposable diapers, wherein the articles do not develop unpleasant smells, wherein the process comprises polymerizing with partial crosslinking, water-soluble ethylenically unsaturated monomers to form a polymeric product;

swelling said polymeric product with an aqueous solution of a boron derivative said boron derivative selected from the group consisting of anhydrous sodium tetraborate, sodium tetraborate pentahydrate, sodium tetraborate decahydrate, and sodium metaborate of any degree of hydration; and removing excess water by evaporation.

2. A process for the production of a superabsorbent composition intended for the production of sanitary articles selected from the group consisting of underwear, diapers and disposable diapers, wherein the articles do not develop unpleasant smells, wherein the process comprises polymerizing with partial crosslinking, water-soluble ethylenically unsaturated monomers to form a polymeric product; and mixing with said polymeric product a borate selected from the group consisting of sodium tetraborate or sodium metaborate, in the proportion 0.1 to 10% by weight of borate, with respect to the superabsorbent composition.

* * * * *

UNITED STATES PATENT AND TRADEMARK OFFICE
CERTIFICATE OF CORRECTION

PATENT NO. : 5,885,263  
DATED : Mar. 23, 1999  
INVENTOR(S) : Gancet et al.

Page 1 of 3

It is certified that error appears in the above-identified patent and that said Letters Patent is hereby corrected as shown below:

The title page should be deleted to appear as per attached title page.

Please insert the following drawing sheet 1 of 1 as per attached.

Signed and Sealed this

Tenth Day of August, 1999

*Attest:*

Q. TODD DICKINSON

*Attesting Officer*    Acting Commissioner of Patents and Trademarks

United States Patent [19]
Gancet et al.

[11] Patent Number: 5,885,263
[45] Date of Patent: Mar. 23, 1999

[54] SUPERABSORBENT COMPOSITION INTENDED FOR THE PRODUCTION OF SANITARY ARTICLES OF THE UNDERWEAR, DIAPER OR DISPOSABLE DIAPER TYPE WHICH DO NOT DEVELOP UNPLEASANT SMELLS

[75] Inventors: Christian Gancet, Lons; Nathalie Cuny, Carrieres/Seine; Monique Lescure, Pau; Jean-Louis Seris, Jurancon, all of France

[73] Assignee: Elf Atochem S.A., Puteaux, France

[21] Appl. No.: 634,716

[22] Filed: Apr. 18, 1996

[30] Foreign Application Priority Data

Apr. 18, 1995 [FR] France .................................. 95 04584

[51] Int. Cl.$^6$ .............................. B32B 5/16; A61F 13/15
[52] U.S. Cl. .................. 604/359; 604/360; 604/368; 424/489; 428/402; 428/403
[58] Field of Search ...................... 604/359, 360, 604/368; 428/402, 403; 424/489

[56] References Cited

U.S. PATENT DOCUMENTS

| | | |
|---|---|---|
| 1,935,170 | 11/1933 | Woody et al. |
| 1,953,526 | 4/1934 | Ainslie et al. |
| 4,333,461 | 6/1982 | Muller. |
| 4,363,322 | 12/1982 | Andersson. |
| 4,624,868 | 11/1986 | Muller. |
| 4,641,605 | 2/1987 | Gordon .................... 119/1 |
| 4,992,326 | 2/1991 | Dabi ...................... 428/283 |
| 5,183,010 | 2/1993 | Raymond et al. ............ 119/172 |
| 5,183,655 | 2/1993 | Stanislowski et al. ........ 424/76.7 |
| 5,230,958 | 7/1993 | Dabi ...................... 428/402 |

FOREIGN PATENT DOCUMENTS

| | | |
|---|---|---|
| 0 164 818 | 12/1985 | European Pat. Off. |
| 61 179 155 | 8/1986 | Japan. |
| WO 94/25077 | 11/1991 | WIPO. |

*Primary Examiner*—John G. Weiss
*Assistant Examiner*—Dennis Ruhl
*Attorney, Agent, or Firm*—Pennie & Edmonds LLP

[57] ABSTRACT

Compositions which greatly diminish, or eliminate, unpleasant smells associated with the use of underwear and diapers are described. These compositions are composed of superabsorbent polymers of the polyacrylic type and of certain boron derivatives, in particular sodium tetraborate. The sanitary articles which incorporate these compositions do not develop unpleasant smells, ammoniacal or otherwise.

2 Claims, 1 Drawing Sheet